United States Patent [19]
Toth

[11] Patent Number: 4,472,431
[45] Date of Patent: Sep. 18, 1984

[54] METHOD FOR TREATMENT OF SHOCK

[75] Inventor: Phillip D. Toth, Lebanon, Ind.

[73] Assignee: Methodist Hospital of Indiana, Inc., Indianapolis, Ind.

[21] Appl. No.: 565,379

[22] Filed: Dec. 27, 1983

Related U.S. Application Data

[63] Continuation-in-part of Ser. No. 524,457, Aug. 18, 1983.

[51] Int. Cl.³ ............................................. A61K 31/19
[52] U.S. Cl. .................................................... 424/317
[58] Field of Search ......................................... 424/317

[56] References Cited

U.S. PATENT DOCUMENTS

| | | | |
|---|---|---|---|
| 4,135,051 | 1/1979 | Walker | 560/100 |
| 4,142,054 | 2/1979 | Amin et al. | 560/105 |
| 4,185,100 | 2/1980 | Rovee et al. | 424/240 |
| 4,267,182 | 5/1981 | Holaday et al. | 424/260 |
| 4,282,214 | 8/1981 | Flora et al. | 424/204 |
| 4,355,029 | 10/1982 | Ridolfo | 424/232 |

*Primary Examiner*—Stanley J. Friedman
*Attorney, Agent, or Firm*—Woodard, Weikart, Emhardt & Naughton

[57] ABSTRACT

A method for the treatment of shock is disclosed which includes the administration of a therapeutically effective amount of fenoprofen, which may be administered either as a pretreatment or subsequent to the onset of the shock condition. The fenoprofen is preferably administered intravenously.

15 Claims, No Drawings

METHOD FOR TREATMENT OF SHOCK

RELATED APPLICATION

The present application is a continuation in part of my copending U.S. patent application Ser. No. 524,457, filed on Aug. 18, 1983.

BACKGROUND OF THE INVENTION

1. Field of the Invention: The present invention relates to the field of methods for the treatment of shock, and more particularly to a method for treating shock by use of drugs.

2. Description of the Prior Art: The term shock is applied to a variety of pathophysiological conditions associated with hypotension. Shock is a condition of acute peripheral circulatory failure due to derangement of circulatory control or loss of circulating fluid and is marked by pallor and claminess of the skin, decreased blood pressure, feeble rapid pulse, decreased respiration, restlessness, anxiety, and sometimes unconsciousness. Some examples are hemorrhagic shock (blood loss), cardiogenic shock (heart attack), endotoxic shock, and septic shock (infection).

In spite of aggressive therapy, the morbidity and mortality rates for shock patients are quite high, in the range of 20–70%. Moreover, this has been a condition which has been extremely difficult to treat. Much research has been conducted in this field in an effort to determine the mechanism of the shock condition and methodologies for satisfactory treatment of shock after its onset.

There has been recent speculation that the body releases certain hormones or mediators which cause the low blood pressure. Many vasoactive mediators have been implicated in the pathophysiology of many shock states including endotoxic shock. The mediators which have received much attention in endotoxic shock have been the opioids, prostanoids, histamine, kinins, serotonin, VIP, etc. However, what has yet to be established is the relative hemodynamic contribution of each of these mediators in a given shock model.

Some drugs are currently being promoted for use in the treatment of shock. Previously, the use of a massive dose of glucocorticoids in a patient with septic shock was being employed. The Food and Drug Administration recently reviewed the indications for the use of corticosteroids in septic shock, in particular for a drug methylprednisolone sodium succinate, and decided to remove septic shock from the product insert as an indication for the use of high doses. The use of this and related drugs for the treatment of shock is discussed in an article entitled "Septic Shock and Corticosteroids", John N. Sheagren, M.D., appearing in The New England Journal of Medicine, pp. 456–7, Aug. 20, 1981.

It has previously been demonstrated that the cyclooxygenase inhibitor, ibuprofen, given 60 minutes after endotoxin administration could improve hemodynamics but not survival over control animals in a canine endotoxic shock model. A paper on this subject entitled "The Effects of Different Vasoactive Mediator Antagonists on Endotoxic Shock in Dogs I" was presented at the Fifth Annual Conference on Shock, at Smugglers' Notch. Vt. on June 9–11, 1982.

A method for the treatment of shock is described in U.S. Pat. No. 4,267,182, issued to Holaday on May 12, 1981. This method includes the administration to the patient of any of a number of drugs including naloxone, naltrexone, nalorphine, diprenorphine, levallorphan, pentazocine, metazocine, cyclazocine, etazocine and the acid addition salts thereof. Each of these drugs is indicated as a narcotic antagonist drug.

The present invention relates to the use of fenoprofen for the treatment of shock. Fenoprofen is a known anti-inflammatory drug which has been available from Eli Lilly & Co. of Indianapolis, Ind. for use in the treatment of arthritis. Other anti-inflammatory drugs and their use are described in U.S. Pat. Nos. 4,355,029, issued to Ridolfo on Oct. 19, 1982; 4,282,214, isued to Flora on Aug. 4, 1981; 4,185,100, issued to Marvel on Jan. 22, 1980; 4,142,054, issued to Amin on Feb. 27, 1979; 4,135,051, issued to Walker on Jan. 16, 1979; and 4,107,439, issued to Salmond on Aug. 15, 1978.

Despite the research conducted in this field, there has remained a strong need for a method for the treatment of shock to both improve hemodynamics and survival. Although various drugs have been investigated for this purpose, the results to date have not been highly successful.

SUMMARY OF THE INVENTION

Briefly describing one aspect of the present invention there is provided a method for the treatment of shock which includes administering to the patient a therapeutically effective amount of fenoprofen.

It is an object of the present invention to provide a method for the treatment of shock.

It is a further object of the present invention to provide a method for treating shock which is successful both in improving hemodynamics and in overall recovery from the condition.

Another object of the present invention is to provide a method of treating shock which is readily followed.

A further object of the present invention is to provide a method for the treatment of shock either by pre-treatment or by treatment late in the condition.

Further objects and advantages of the present invention will become apparent from the description of the preferred embodiment which follows.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the described process, and such further applications of the principles of the invention as illustrated therein being contemplated as would normally occur to one skilled in the art to which the invention relates.

The present invention involves the treatment of shock by the administration of fenoprofen in a therapeutically effective amount. As will be indicated in the specific examples to follow, it has been found that the administration of such drug has resulted in both improved hemodynamics and increased survival. These results evidence a remarkable impact of the use of this drug in the treatment of a condition which has been a severe problem.

Fenoprofen is a drug which is known in the industry, and in the past has been indicated primarily for its efficacy as an anti-inflammatory. This drug consequently has been available to the field in varying administration forms and dosages, and the preparation of such is therefore not considered necessary in this description relating to a use for such drug. It is noted that this drug is readily soluble, and its preparation in IV form is therefore easily accomplished by usual techniques known to persons skilled in the art.

It is interesting to note the currently perceived mechanism associated at least in part with the shock condition. Although not intended in any way as a limitation of the present invention, the potential relationship with the operation of fenoprofen will be discussed.

There is a recognized mechanism known as the protaglandin cascade or arachidonic acid cascade which leads to the release of several different compounds within the body. This cascade begins with the presence of inaccessible phospholipids within the body. Upon stimulus, these phospholipids convert to a form in which they are accessible, and such conversion is believed to be inhibited by glucocorticoids. Thus, certain glucocorticoids have been investigated for counteracting the development of this cascade, although with doubtful success as indicated earlier.

The accessible phospholipids are available to be acted upon by phospholipase for conversion into arachidonic acid. This acid in turn may yield several additional compounds along one of at least two pathways. Conversion by lipoxygenase results in the production of leukotrienes, 5,15 HPETE and 12-HPETE. Several other compounds result from the operation of cyclo-oxygenase on the arachidonic acid in the presence of oxygen to form $PGG_2$, convertible in turn to $PGH_2$, prostacyclin, thromboxane $A_2$, etc.

In the past, it has been considered to use inhibitors to the cyclo-oxygenase pathway in shock. One such example is ibuprofen, discussed earlier. However, the results have been typically reported as improving hemodynamics, but not mortality.

Prior studies have demonstrated in a canine endotoxic shock model ($LD_{100}$) that the selective cyclo-oxygenase inhibitor, ibuprofen, given 60 minutes after endotoxin administration, could improve hemodynamics within 30-60 minutes, but did not improve survival over control animals. Naloxone administration has demonstrated only transient hemodynamic improvement. These and other data suggest that the products of the prostaglandin cascade are probably more hemodynamically important than the opioids as vasoactive mediators in this type of canine endotoxic shock. Leukotrienes, products of the lipoxygenase pathway, have also been implicated as important vasoactive mediators in the endotoxic (septic) shock syndrome. When given systemically, they can cause hypotension, can increase vascular permeability, and can decrease myocardial contractility which are characteristic features of shock.

Many vasoactive mediators have been implicated in causing or maintaining the hypotension in hemorrhagic shock. The present invention utilizes fenoprofen, a selective cyclo-oxygenase inhibitor, in the treatment of hemorrhagic shock, and in one aspect has been examined particularly on a canine hemorrhagic shock model.

After thiopental anesthesia, animals were instrumented to measure various cardiovascular parameters. All animals were bled to and maintained at a mean arterial pressure (MAP) of 60 mmHg for 90 minutes. After the shock period, animals were then given fenoprofen (10 mg/kg) (n=9) or an equivalent volume of saline (n=6). After another 90 minutes observation period, the shed blood was reinfused. A significant increase of MAP was noted in the fenoprofen group secondary to an increase of total peripheral resistance (TPR).

In another aspect, the present invention includes the use of fenoprofen, a selective cyclo-oxygenase inhibitor in the treatment of endotoxic shock, and in one example demonstrates the use of fenoprofen in the canine endotoxic shock model.

After thiopental anesthesia (25 mg/kg i.v.), animals were instrumented to measure various cardiovascular parameters. Endotoxic shock was induced by injecting E. coli ($0111:B_4$) endotoxic (1 mg/kg i.v.). Fenoprofen (1 mg/kg i.v.) (n=5), fenoprofen (10 mg/kg) (n=6), or saline (n=12) was injected 60 minutes after endotoxin administration. During the treatment period, both doses of fenoprofen increased mean arterial pressure, $dP/dt_{max}$, heart rate, and vascular resistance in a dose-response manner over the control animals. Twenty-four hour survival was 0% for the control animals (n=12), 60% for the fenoprofen group (1 mg/kg) and 61% for the fenoprofen (10 mg/kg) group. These data demonstrate that fenoprofen improves survival in an otherwise lethal endotoxic shock model.

EXAMPLE I

Healthy, adult male beagles weighing 10–15 kg were anesthetized with thiopental (25 mg/kg) i.v. two days prior to each experiment. They were then shaved and depilated in the neck, mid-thorax, and femoral areas and allowed to spontaneously recover. On the day of the experiment, each dog was again anesthetized with thiopental (25 mg/kg i.v.), intubated with a cuffed endotracheal tube, and allowed to breath spontaneously on room air. Additional small doses of thiopental (1–2 mg/kg) were administered when necessary. On the shaved areas, the impedance electrode tape was placed circumferentially in the usual manner.

In the neck, the right jugular vein was exposed and a Swan-Ganz catheter was inserted to measure mean pulmonary artery pressure (PAP) and mean pulmonary artery wedge (PAW) pressure. Also through the same neck approach, a "pigtail" catheter was inserted into the left ventricle to measure $dP/dt_{max}$.

In the left groin area, the femoral artery was exposed and a 7F catheter was inserted and connected to a transducer to measure arterial pressure (MAP). In the right groin area, the femoral artery was exposed and a 7F catheter was inserted and connected to a blood bag (Fenwal Laboratories, Deerfield, Ill.) for hemorrhaging the animal. All pressures were measured with Gould-Statham P23Db pressure transducers, which were calibrated daily.

Other cardiodynamics were measured by a Minnesota Impedance Cardiograph (Model 304B) (Surcom, Inc., Minneapolis, MN) which is a tetrapolar electrode system. The outer two leads (1 and 4) were connected to an oscillator which produced a 100 kH, 4 ma constant current and detected an EKG signal. The inner two electrodes were connected to an Impedance Cardiograph Microcomputer (Model 700) (Surcom, Inc., Minneapolis, MN) which measured on a beat-by-beat basis, heart rate (HR), stroke volume (SV), cardiac output (CO), and the Heather Index (HI) (a measurement of contractility). It has been demonstrated in the past that CO measured by impedance is equivalent to CO determined by the thermodilution or dye dilution methods. Recent work has demonstrated a correlation coefficient of r=0.88 for SV determined by impedance and thermodilution during the pre-shock and shock periods of an endotoxin model.

Total peripheral resistance (TPR) was calculated from the following formula: TPR:=MAP/CO. Pulmonary vascular resistance (PVR) was calculated from the formula: PVR=PAP-PAW/CO. Ejection fraction (EF) was calculated from a standard impedance signal using the method of Judy which has been shown to be equivalent to single-pass radionuclide or ventriculogram methods. End diastolic volume was calculated as follows: EDV=SV/EF. All impedance data and pressures were recorded simultaneously on a Beckman Type R Dynograph.

After all surgery was completed, each dog was given heparin (10,000 U i.v.). After a 15 minute baseline period, the animals were bled to a MAP of 60 mmHg over a 30 minute period. This pressure was maintained for another 60 minutes at this level by raising or lowering the blood bag as needed.

After the 90 minutes of shock, the animals were given either fenoprofen (10 mg/kg) (n=9) or an equal volume of saline (n=6) intravenously. After another 90 minutes observation period, the shed blood was reinfused in both groups and observed for another 45 minutes. After this last observation period, the catheters were removed, the vessels ligated, and the animals were returned to their cages. Animals were observed every 12 hours until death and then autopsied.

STATISTICAL ANALYSIS

Data was analyzed using paired Student t-tests, two group Student Fisher's exact test, and repeated measures analysis of variance. A p-value of $\leq 0.05$ was considered significant.

RESULTS

Analysis of data during the pre-shock and shock periods demonstrated no significant statistical differences (p≦0.05) between the groups except for PAP and PVR in the hemorrhage period for the fenoprofen group. Fenoprofen (10 mg/kg) given to instrumented, non-shocked animals had no effect on hemodynamics. FIG. 1 demonstrates the increase of MAP after fenoprofen administration. There was no increase of HR, SV, CO, EDV, HI, or $dP/dt_{max}$ to account for the increase of MAP (FIGS. 2-8). The parameter which did increase to account for the increase of MAP was TPR (FIG. 9). Even though PAP and PVR was elevated during the shock period in the fenoprofen group, there was no increase after fenoprofen administration. Survival at 48 hours was 50% (3/6) in the control group and 100% (9/9) in the fenoprofen group (Table 1).

TABLE 1

| TIME | SURVIVAL | |
|---|---|---|
| | CONTROL (n = 6) | FENOPROFEN (n = 9) |
| 24 hours | 3 | 9 |
| 48 hours | 3 | 9 |

DISCUSSION

Recent work in shock research has implicated many circulating vasoactive mediators as important contributors to the pathophysiology of shock. The present study examined the effects of a prostaglandin inhibitor on the hemodynamics of a prolonged hemorrhagic shock model in dogs. The data demonstrated that fenoprofen, a selective cyclo-oxygenase inhibitor, increased MAP secondary to a rise of TPR. In summary, fenoprofen, a cyclo-oxygenase inhibitor, increases hemodynamics in a hemorrhagic shock model by increasing vascular resistance.

EXAMPLE II

Healthy adult male hounds weighing 20-25 kg were anesthetized with thiopental (25 mg/kg) i.v. two days prior to each experiment. They were then shaved and depilated in the neck, mid thorax, and femoral areas, and allowed to spontaneously recover. On the day of the experiment, each dog was again anesthetized with thiopental (25 mg/kg i.v.), intubated with a cuffed endotracheal tube, and allowed to breath spontaneously on room air. Additional small doses of thiopental (1-2 mg/kg) were administered when necessary. On the shaved areas, the impedance electrode tape was placed circumferentially in the usual manner.

In the neck, the right jugular vein was exposed and a Swan-Ganz catheter was inserted to measure mean pulmonary artery pressure (PAP) and mean pulmonary artery wedge (PAW) pressure. Also through the same neck approach, a "pigtail" catheter was inserted into the left ventricle to measure $dP/dt_{max}$.

In the left groin area, the femoral artery was exposed and a 7F catheter was inserted and connected to a transducer to measure mean arterial pressure (MAP). All pressures were measured with Gould-Statham P23Db pressure transducers which were calibrated daily.

Other cardiodynamics were measured by a Minnesota Impedance Cardiograph (Model 304B) (Surcom, Inc., Minneapolis, MN) which is a tetrapolar electrode system. The outer two leads (1 and 4) were connected to an oscillator which produced a 100 kHz, 4 ma constant current and detected an EKG signal. The inner two electrodes were connected to an Impedance Cardiograph Microcomputer (Model 7000) (Surcom, Inc., Minneapolis, MN) which measured on a beat-by-beat basis, heart rate (HR), stroke volume (SV), cardiac output (CO), and Heather Index (HI) (a measurement of contractility). It has been demonstrated in the past that CO measured by impedance is equivalent to CO determined by the thermodilution or dye dilution methods. Recent work has demonstrated a correlation coefficient of r=0.88 for SV determined by impedance and thermodilution during the pre-shock and shock periods for this $LD_{100}$ canine endotoxic shock model. Total peripheral resistance (TPR) was calculated by the following formula: TPR=MAP/CO.

Ejection fraction (EF) was calculated from a standard impedance signal using the method of Judy which has been shown to be equivalent to single-pass radionuclide or ventriculogram methods. End diastolic volume was calculated as follows: EDV=SV/EF.

All impedance data and pressures were recorded simultaneously on a Beckman Type R Dynograph. After all surgery was completed, each dog was given heparin (10,000 U i.v.). After a 30 minute baseline period, each dog was given endotoxin (1 mg/kg i.v.) (E. coli 011:B4) (Difco). Sixty minutes after endotoxin administration, fenoprofen (1 mg/kg), fenoprofen (10 mg/kg) or an equivalent volume of saline was injected intravenously. Animals were physiologically monitored for an additional 2½ hours. The catheters were then removed, and the animals were returned to their cages. Animals were observed until death and then were autopsied.

STATISTICAL ANALYSIS

Data was analyzed using paired Student t-tests and repeated measures analysis of variance. Mortality data was analyzed using the Fisher's exact test. A p-value of $\leq 0.5$ was considered significant.

RESULTS

Comparison of the groups demonstrated no significant differences for any of the parameters during the baseline and the shock periods (FIGS. 10-20). No hemodynamic changes were noted when fenoprofen was administered to instrumented non-shocked animals. At time 0, endotoxic shock was induced by injecting endotoxin (E. coli 0111:B4) (1 mg/kg i.v.). Sixty minutes after endotoxin administration, fenoprofen at two different doses or an equivalent volume of saline was administered. FIGS. 10-20 illustrate the typical hemodynamic profile after endotoxin administration for our model. This consists of essentially three phases: (1) early, rapid hypotension, (2) transient compensatory phase, (3) late hypotension.

FIG. 10 demonstrates that both doses of fenoprofen were equally effective in increasing MAP to near pre-shock levels. The group given a lower dose of fenoprofen (1 mg/kg) demonstrated an increase of CO and EDV late in the treatment period while the group given the larger dose did not (FIGS. 11-15). These minor changes in CO and EDV in the one group and no comparable changes in the group given the larger dose of fenoprofen could not account for the increase of MAP in both treatment groups. With regards to contractility, there was a dose-response increase in $dp/dt_{max}$ in the fenoprofen groups (FIG. 17). HI, the impedance contractility index, demonstrated no improvement in either fenoprofen group (FIG. 16). The parameter with the most improvement to account for the increase of MAP was TPR which was improved in a dose response manner in the fenoprofen groups (FIG. 18).

Survival at 24 hours was 0% (0/12) for the control group, 60% (3/5) for the fenoprofen (1 mg/kg) group, and 67% (4/6) for the fenoprofen (10 mg/kg) group (Table II).

TABLE II

| 24 HOUR SURVIVAL | | |
|---|---|---|
| CONTROL | 0/12 | p value |
| FENOPROFEN | | |
| 1 mg/kg | 3/5 | .015 |
| 10 mg/kg | 4/6 | .005 |

DISCUSSION

The present study illustrates that the administration of fenoprofen, a selective cyclo-oxygenase inhibitor, not only improves hemodynamics, but also extends survival in an otherwise lethal canine endotoxic shock model. Both doses of fenoprofen increased MAP, $dp/dx_{max}$, and vascular resistance (TPR and PVR) in a dose-response manner. There were minor changes noted between the two groups. The lower dose of fenoprofen demonstrated some minor improvement of CO and EDV late in the treatment period. The increase, however, could not account for the increase of MAP. The major parameter increase to account for the increase of MAP in both groups was vascular resistance. There was an increase of $dp/dt_{max}$ in both treatment groups. However, HI, the impedance contractility index, demonstrated no improvement. Since various contractility indices can be affected by preload or afterload, one cannot always accurately assess the true contractility characteristics of the myocardium in pathologic states.

It has therefore been shown that the administration of fenoprofen will effectively treat the shock condition when given in therapeutic amounts. Fenoprofen is also appropriate for the pretreatment of patients considered to have a high risk of infection (e.g. surgery) or to prevent other types of potential shock situations. Pretreatment is appropriate, for example, for hospitalized patients, particularly for patients who have suffered a significant loss of blood or have a potential for additional blood loss, or having a high risk or potential for shock. In particular, the administration of the drug desirably within an hour or two before the onset of the shock condition improves hemodynamics and increases the chances of survival from the shock condition. A further example of a pretreatment situation would be in the administration of fenoprofen to a person prior to the person undergoing a surgical procedure, which would put the person at high risk for severe blood loss or infection.

The fenoprofen may be administered in a variety of manners, typically depending on the circumstances of administration. The drug may for example be administered parenterally, and preferably intravenously.

EXAMPLE III

Impedance cardiography and invasive methods were used to measure various cardiovascular parameters. Dogs (beagles) were anesthetized with thiopental (25 mg/kg i.v.), intubated, and allowed to breathe spontaneously. Endotoxic shock was induced by injecting E. coli (0111:B4) endotoxin (1 mg/kg i.v.). Fenoprofen (10 mg/kg) (n=6) or saline (n=6) was injected 120 minutes after endotoxin administration. Pre-shock and shock hemodynamics between the two groups showed no significant differences. During the treatment period, no differences between the two groups were noted for heart rate, stroke volume, cardiac output (CO), end diastolic volume, dP/dt, and pulmonary artery wedge pressure. However, in the fenoprofen group, there was a sustained improvement in mean arterial pressure (MAP) and total peripheral resistance (TPR). Representative data (mean+/−SEM) observed two hours after drug administration are listed in Table III. Twenty-four hour survival for the control group was 0% (0/6) versus 100% (6/6) for the fenoprofen group.

TABLE III

| | Control | Fenoprofen |
|---|---|---|
| MAP | 77.4 +/− 7.9 | 150 +/− 4.5* |
| CO | 3.37 +/− 0.46 | 2.30 +/− 0.38 |
| TPR | 24.8 +/− 4.2 | 76.6 +/− 16.9* |

*$p \leq 0.05$

These data indicate that delayed intervention (two hours) with fenoprofen can still improve survival in an otherwise $LD_{100}$ endotoxic shock model.

What I claim is:

1. A method for the treatment of shock which comprises administering parenterally to a person suffering from shock a therapeutically effective amount of fenoprofen.

2. The method of claim 1 in which the fenoprofen is administered within two hours after onset of the shock condition.

3. The method of claim 1 in which the fenoprofen is administered intravenously.

4. The method of claim 3 in which the fenoprofen is administered within two hours after onset of the shock condition.

5. A method for the treatment of a person having a potential for the onset of a shock condition, which method comprises administering parenterally to the person having the potential for the onset of shock a therapeutically effective amount of fenoprofen.

6. The method of claim 5 in which the fenoprofen is administered to a person having a high risk of the onset of shock.

7. The method of claim 5 in which the fenoprofen is administered to a hospitalized patient.

8. The method of claim 7 in which the patient has a high risk of the onset of shock.

9. The method of claim 5 in which the fenoprofen is administered to a person who has recently suffered a significant loss of blood.

10. The method of claim 5 in which the fenoprofen is administered to a person having a high risk of infection.

11. The method of claim 10 in which the person is a hospitalized patient.

12. The method of claim 5 in which the fenoprofen is administered to a hospitalized patient prior to the patient's undergoing a surgical procedure.

13. The method of claim 12 in which the fenoprofen is administered to the patient within an hour before the surgical procedure.

14. The method of claim 12 in which the surgical procedure subjects the patient to a high risk of infection.

15. The method of claim 12 in which the surgical procedure subjects the patient to a high risk of a significant blood loss.

* * * * *